United States Patent [19]
Jakobovits et al.

[11] Patent Number: 6,130,364
[45] Date of Patent: *Oct. 10, 2000

[54] PRODUCTION OF ANTIBODIES USING CRE-MEDIATED SITE-SPECIFIC RECOMBINATION

[75] Inventors: Aya Jakobovits, Menlo Park; Krisztina M. Zsebo, Woodside, both of Calif.

[73] Assignees: Abgenix, Inc., Fremont, Calif.; Japan Tobacco Inc., Tokyo, Japan

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/412,826

[22] Filed: Mar. 29, 1995

[51] Int. Cl.$^7$ .......................... C12N 15/85; C12N 15/00; A01K 67/00

[52] U.S. Cl. ................. 800/6; 800/13; 800/18; 800/4; 435/463; 435/69.1; 435/326

[58] Field of Search ............... 435/172.3, 240.1, 435/69.1, 254, 320.1, 91.1, 192.3, 462, 463, 326; 536/23.2, 23.1; 800/13, 18, 21, 4, 6

[56] References Cited

U.S. PATENT DOCUMENTS

| | | | |
|---|---|---|---|
| 4,816,567 | 3/1989 | Cabilly et al. | 530/387 |
| 4,959,317 | 9/1990 | Sauer | 435/172.3 |
| 5,202,238 | 4/1993 | Fell et al. | 435/69.6 |
| 5,434,066 | 7/1995 | Beebe et al. | 435/172.3 |
| 5,434,340 | 7/1995 | Krimpenfort et al. | 800/2 |
| 5,545,806 | 8/1996 | Lonberg et al. | 800/2 |

FOREIGN PATENT DOCUMENTS

| | | | |
|---|---|---|---|
| WO 86/01533 | 3/1986 | WIPO | C12N 15/00 |
| WO 91/10741 | 7/1991 | WIPO | C12P 21/06 |
| WO 93/19172 | 9/1993 | WIPO | C12N 15/00 |
| WO 94/02602 | 2/1994 | WIPO | C12N 15/00 |
| WO 94/04667 | 3/1994 | WIPO | C12N 15/00 |

OTHER PUBLICATIONS

Zou et al. (1994) Current Biology, vol. 4 (12), 1099–1103.
Kohler et al. (1975) Nature, vol. 256, 495–497.
Miller et al. (1995) FASEB, vol. 9, 190–199.
Campbell et al. (1997) Theriology, vol. 47 (1), 63–72.
Zou et al. Current Biology, vol. 4, No. 12, pp. 1099–1103, 1994.
Southern & Berg, "Transformation of Mammalian Cells to Antibioic Resistance with a Bacterial Gene Under Control of the SV40 Early Region Promoter," J. Mol. Appl. Genet. 1:327–341 (1982).
Ito et al., "Solid phase synthesis of polynucleotides. VI. Further studies on polystyrene copolymers for the solid support," Nuc. Acids Res. 10:1755–1769 (1982).
Spira et al., "The Identification of Monoclonal Class Switch Variants by Sib Selection and an ELISA Assay," J. Immunological Methods 74:307–315 (1984).
Neuberger et al., "Recombinant antibodies possessing novel effector functions," Nature 312:604–608 (1984).
Blochlinger & Diggelmann, "Hygromycin B Phosphotransferase as a Selectable Marker for DNA Transfer Experiments with Higher Eucaryotic Cells," Mol. Cell Biol., 4:2929–2931 (1984).
Tan et al., "A Human'Mouse Chimeric Immunoglobulin Gene with a Human Variable Region is Expressed in Mouse Myeloma Cells," J. Immunol. 135:3564–3567 (1985).
Waterhouse et al., "Combinatorial infection and in vivo recombination: a strategy for making large phage antibody repertoires," Nucleic Acids Res. 21:2265–2266 (1993).
Steplewski et al., "Isolation and characterization of anti-–monodialoganglioside monoclonal antibody 19–9 class–switch variants," Proc. Natl. Acad. Sci. USA 82:8653–8657 (1985).
Gu et al., "Independent Control of Immunoglobulin Switch Recombination at Individual Switch Regions Evidenced through Cre–LoxP–Mediated Gene Targeting," Cell 73:1155–1164 (1993).
Hoess et al., "P1 site–specific recombination: Nucleotide sequence of the recombing sites," Proc. Natl. Acad. Sci. USA 79:3398–3402 (1982).
Graham et al., "A New Technique for the Assay of infectivity of Human Adenovirus 5 DNA," Virology 52:456–467 (1973).
Pavlakis et al., "Regulation of a metallothionein–growth hormone hybrid gene in bovine papilloma virus," Proc. Natl. Acad. Sci. USA 80:397–401 (1983).
Gorman et al., "The Rous sarcoma virus long terminal repeat is a strong promoter when introduced into a variety of eukaryotic cells by DNA–mediated transfection," Proc. Natl. Acad. Sci. USA 79:6777–6781 (1982).
Alvarado–Urbina et al., "Automated Synthesis of Gene Fragments", Science, 214:270–274 (1981).
Capecchi, M.R., 1989. "Altering the Genome by Homologous Recombination." *Science* 244:1288–92.

Primary Examiner—Karen M. Hauda
Assistant Examiner—AnneMarie S. Beckerleg
Attorney, Agent, or Firm—Carol L. Francis; Paula A. Borden; Bozicevic, Field & Francis LLP

[57] ABSTRACT

A method to produce a cell expressing an antibody from a genomic sequence of the cell comprising a modified immunoglobulin locus using Cre-mediated site-specific recombination is disclosed. The method involves first transfecting an antibody-producing cell with a homology-targeting vector comprising a lox site and a targeting sequence homologous to a first DNA sequence adjacent to the region of the immunoglobulin loci of the genomic sequence which is to be converted to a modified region, so the first lox site is inserted into the genomic sequence via site-specific homologous recombination. Then the cell is transfected with a lox-targeting vector comprising a second lox site suitable for Cre-mediated recombination with the integrated lox site and a modifying sequence to convert the region of the immunoglobulin loci to the modified region. This conversion is performed by interacting the lox sites with Cre in vivo, so that the modifying sequence inserts into the genomic sequence via Cre-mediated site-specific recombination of the lox sites. Also disclosed are a form of the method used to produce a cell expressing a modified antibody molecule using Cre-mediated site-specific recombination, and antibody-producing cells obtainable by the disclosed methods. Class-switching modifications of human antibodies produced in murine hybridoma cells are exemplified.

27 Claims, 3 Drawing Sheets

PRODUCTION OF ANTIBODIES USING CRE-MEDIATED SITE-SPECIFIC RECOMBINATION

TECHNICAL FIELD

The invention relates to a process to produce antibodies from genetic loci modified using recombinant DNA vectors and site-specific recombination leading to the production of modified antibody molecules by transfected cells. More particularly, the invention relates to the use of Cre-mediated site-specific recombination for modifying immunoglobulin loci, for instance, to replace all or a portion of either the constant region or variable region of an antibody molecule to form a modified antibody molecule. One particular aspect relates to class-switching of antibody genes in antibody-producing lymphoid cells in situ whereby a constant region of an immunoglobulin gene is replaced with a constant region of another class, thereby producing a modified antibody with a changed isotype. Another aspect relates to modification of the variable region, or a portion thereof, which is replaced or exchanged with a variable region having a different or altered antigen specificity.

BACKGROUND ART

The basic immunoglobulin structural unit in vertebrate systems is composed of two identical "light" polypeptide chains of molecular weight approximately 23,000 daltons, and two identical "heavy" chains of molecular weight 53,000–70,000. The four chains are joined by disulfide bonds in a "Y" configuration in which the light chains bracket the heavy chains starting at the mouth of the Y and continuing through the divergent region or "branch" portion which is designated the Fab region. Heavy chains are classified as gamma ($\gamma$), mu ($\mu$), alpha ($\alpha$), delta ($\delta$), or epsilon ($\epsilon$), with some subclasses among them which vary according to species; and the nature of this chain, which has a long constant region, determines the "class" of the antibody as IgG, IgM, IgA, IgD, or IgE, respectively. Light chains are classified as either kappa ($\kappa$) or lambda ($\lambda$). Each heavy chain class can be associated with either a kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

The amino acid sequence of each immunoglobulin chain runs from the N-terminal end at the top of the Y to the C-terminal end at the bottom. The N-terminal end contains a variable region (V) which is specific for the antigen to which it binds and is approximately 100 amino acids in length, there being variations between light and heavy chain and from antibody to antibody. The variable region is linked in each chain to a constant region (C) which extends the remaining length of the chain. Linkage is seen, at the genomic level, as occurring through a linking sequence known as the joining (J) region in the light chain gene, which encodes about 12 amino acids, and as a combination of diversity (D) region and joining (J) region in the heavy chain gene, which together encode approximately 25 amino acids. The remaining portions of the chain, the constant regions, do not vary within a particular class with the specificity of the antibody (i.e., the antigen to which it binds). The constant region or class determines subsequent effector function of the antibody, including activation of complement and other cellular responses, while the variable region determines the antigen with which it will react.

Since the development of the cell fusion technique for the production of monoclonal antibodies by Kohler and Milstein, many individual immunoglobulin species have been produced in quantity. Most of these monoclonal antibodies are produced in a murine system and, therefore, have limited utility as human therapeutic agents unless modified in some way so that the murine monoclonal antibodies are not "recognized" as foreign epitopes and "neutralized" by the human immune system.

One approach to this problem has been to attempt to develop human or "humanized" monoclonal antibodies, which are "recognized" less well as foreign epitopes and may overcome the problems associated with the use of monoclonal antibodies in humans. Applications of human B cell hybridoma-produced monoclonal antibodies hold great promise for the treatment of cancer, viral and microbial infections, B cell immunodeficiencies with diminished antibody production, and other diseases and disorders of the immune system.

However, several obstacles exist with respect to the development of human monoclonal antibodies. For example, with respect to monoclonal antibodies which recognize human tumor antigens for the diagnosis and treatment of cancer, many of these tumor antigens are not recognized as foreign antigens by the human immune system and, therefore, these antigens may not be immunogenic in man.

Another problem with human monoclonal antibodies is that most such antibodies obtained in cell culture are of one class or isotype, the IgM type. Under certain circumstances, monoclonal antibodies of one isotype might be more preferable than those of another in terms of their diagnostic or therapeutic efficacy since, as noted above, the isotype determines subsequent effector function of the antibody, including activation of complement and other cellular responses. For example, from studies on antibody-mediated cytolysis it is known that unmodified mouse monoclonal antibodies of subtype $\gamma 2a$ and $\gamma 3$ are generally more effective in lysing target cells than are antibodies of the $\gamma 1$ isotype. This differential efficacy is thought to be due to the ability of the $\gamma 2a$ and $\gamma 3$ subtypes to more actively participate in the cytolytic destruction of the target cells. Particular isotypes of a murine monoclonal antibody can be prepared either directly, by selecting from the initial fusion, or secondarily, from a parental hybridoma secreting monoclonal antibody of a different isotype, by using the "sib selection" technique to isolate class-switch variants (Steplewski et al., 1985, *Proc. Natl. Acad. Sci. USA* 82:8653; Spira et al., 1984, *J Immunological Methods* 74:307.

When human monoclonal antibodies of the IgG type are desired, however, it has been necessary to use such tedious techniques as cell sorting, to identify and isolate the few cells which are producing antibodies of the IgG or other type from the majority producing antibodies of the IgM type. A need therefore exists for an efficient method of switching antibody classes in isolated antibody-producing cells for any given antibody of a predetermined or desired antigenic specificity.

Various solutions to these problems with monoclonal antibodies for human use have been developed based on recent methods for the introduction of DNA into mammalian cells to obtain expression of immunoglobulin genes, particularly for production of chimeric immunoglobulin molecules comprising a human and a non-human portion. More specifically, the antigen combining (variable) region of the chimeric antibody is derived from a non-human source (e.g., murine), and the constant region of the chimeric antibody (which confers biological effector function to the immunoglobulin) is derived from a human source. Such "humanized" chimeric antibodies should have the antigen binding specificity of the non-human antibody molecule and the effector function conferred by the human antibody molecule.

Generally, chimeric antibodies have been produced conventionally by procedures comprising the following steps (although not necessarily in this order): (1) identifying and cloning the gene segment encoding the antigen binding portion of the antibody molecule; this gene segment (VDJ for heavy chains or VJ for light chains, or more simply, the variable region) may be obtained from either a cDNA or genomic source; (2) cloning the gene segments encoding the constant region or desired part thereof; (3) ligating the variable region with the constant region so that the complete chimeric antibody is encoded in a transcribable and translatable form; (4) ligating this construct into a vector containing a selectable marker and appropriate gene control regions; (5) amplifying this construct in bacteria; (6) introducing the DNA into eukaryotic cells (by transfection), most often cultured mammalian cells such as lymphocytes; (7) selecting for cells expressing the selectable marker; (8) screening for cells expressing the desired chimeric antibody; and (9) testing the antibody for appropriate binding specificity and effector functions.

Antibodies of several distinct antigen binding specificities have been manipulated by these procedures to produce chimeric proteins. In addition several different effector functions have been achieved by linking new sequences to those encoding the antigen binding region. Some of these include enzymes (Neuberger et al., 1984, *Nature* 312:604), immunoglobulin constant regions from another species and constant regions of another immunoglobulin chain (Sharon et al., 1984, *Nature* 309:364; Tan et al., 1985, *J. Immunol.* 135:3565–3567). Neuberger et al., PCT Publication WO 86/01533 (1986) also discloses production of chimeric antibodies and mentions, among the technique's many uses, the concept of "class switching."

Cabilly, et al., U.S. Pat. No. 4,816,567 issued Mar. 28, 1989, describes altered and native immunoglobulins, including constant-variable region chimeras, which are prepared in recombinant cell culture. The immunoglobulins contain variable regions which are immunologically capable of binding predetermined antigens. The vectors and methods disclosed are suitable for use in various host cells including a wide range of prokaryotic and eukaryotic organisms.

Fell et al., U.S. Pat. No. 5,202,238 issued Apr. 13, 1993, describes a process for producing chimeric antibodies using recombinant DNA vectors and homologous recombination in vivo. The process uses novel recombinant DNA vectors to engineer targeted gene modification accomplished via homologous recombination in either (a) cell lines that produce antibodies having desired antigen specificities, so that the antigen combining site of an antibody molecule remains unchanged, but the constant region of the antibody molecule, or a portion thereof, is replaced or modified; or (b) cell lines that produce antibodies of desired classes which may demonstrate desired effector functions, so that the constant region of an antibody molecule remains unchanged, but the variable region of the antibody molecule or a portion thereof, is replaced or modified. The reported efficiency of recombination was relatively low, however, ranging from 0.39% to 0.75% in several attempts to replace a mouse heavy chain constant region with a human counterpart, even when a selectable marker gene was used to recover recombinant genomes.

Kucherlapati et al., in PCT Publication WO91/10741 (published Jul. 25, 1991) and in PCT Publication WO 94/02602 (published Feb. 3, 1994) disclose xenogeneic specific binding proteins or antibodies produced in a non-primate viable mammalian host by immunization of the mammalian host with an appropriate immunogen. In particular these publications disclose production of antigen-specific human monoclonal antibodies from mice engineered with loci for human immunoglobulin heavy and light chains using yeast artificial chromosomes (YACs). Such mice produce completely human antibodies in response to immunization with any antigen normally recognized by the mouse immune system, including human antigens; and B-cells from these mice are used to make hybridomas producing human monoclonal antibodies via conventional hybridoma production methods. While production of completely human antibodies from transgenic murine hybridomas solves many of the previous problems of producing human monoclonal antibodies, it may be desirable to modify the loci in the cells which produce the antibodies, for instance, to enhance expression or to alter an effector function.

Sauer et al, U.S. Pat. No. 4,959,317, issued Sep. 25, 1990, describes a method for producing site-specific recombination of DNA in eukaryotic cells at sequences designated lox sites. DNA sequences comprising first and second lox sites are introduced into eukaryotic cells and interacted with a recombinase designated Cre (typically, by transient expression of the recombinase from a plasmid), thereby producing recombination at the lox sites. Exemplified eukaryotic cells included yeast cells and monolayer cultures of a mouse cell line. Frequencies of Cre-mediated recombination ranged from 2–3% to 22% for repeated recombination attempts between an exemplary virus and a plasmid, and 98% for the case of deletion of a yeast leu2 gene flanked by lox sites. However, neither recombination in lymphoid cells nor manipulation of immunoglobulin loci is disclosed by Sauer et al.

Gu et al., 1993, *Cell* 73:1155–1164 describes a method to generate a mouse strain in which the J region and the intron enhancer in the heavy-chain locus are deleted from embryonic stem cells using Cre-mediated site-specific recombination. They then analyzed the immunoglobulin isotypes formed by recombination in heterozygous mutant B cells, activated with LPS plus IL4. The authors used Cre-mediated site-specific recombination merely to modify the heavy chain locus in stem cells which are not antibody-producing cells, and only to modify that locus by deletion, rather than to produce new combinations of gene sequences in antibody-producing cells to produce chimeric or modified antibodies.

Johnson et al., in PCT Publication WO93/19172 (published Sep. 9, 1993), and Waterhouse et al., in the journal article, *Nucleic Acids Res* (1993) 21:2265–2266, describe use of Cre-mediated site-specific recombination to effect recombinations for creation of a combinatorial library of antibodies in phage vectors. In the latter publication, Johnson, Waterhouse and coworkers describe two exemplary phage vectors designated A and B, where A encodes the light chain of a first antibody (and the heavy chain from a different antibody) and B encodes the heavy chain of the first antibody. In both vectors the variable heavy chain (VH) genes are flanked by two loxP sites, one of which is a mutant loxP site which prevents recombination within the vector from merely excising the VH genes. When Cre recombinase is provided in vivo by infecting the *E. coli* with a phage expressing Cre, vectors A and B can co-integrate by recombination between either mutant or wild-type loxP sites to create chimeric plasmids. Further recombination can then occur between the two wild-type or the two mutant loxP sites, to generate original vectors A and B or two new vectors, E and F. The heavy chains of A and B are therefore exchanged in E and F, and E encodes the Fab fragment of the first antibody for display as a fusion to the N-terminus of the phage gene 3 protein (g3p). The authors indicate that the method should allow the creation of extremely large combinatorial repertoires of phage-expressing antibodies, for example by providing a light chain repertoire in phage vector A and a heavy chain repertoire in phage vector B. However, these two publications do not disclose use of Cre-mediated site-specific recombination for any other purpose besides exchange of heavy chain genes in the particular bacteriophage vectors disclosed and, more specifically, do not propose any modification of immunoglobulin sequences in the genome of any antibody-producing cell.

Accordingly, the present invention provides for a novel use of Cre-mediated site-specific recombination for modification of immunoglobulin loci in the cellular genome of any antibody-producing cell.

DISCLOSURE OF THE INVENTION

The invention is directed to processes for producing a cell expressing a desired antibody from a genomic sequence by modification of an immunoglobulin locus using Cre-mediated site-specific recombination. The methods provide, inter alia, the advantage of increased efficiency of recombination over previous methods of modifying immunoglobulin loci directly in antibody-producing cells using only homologous recombination for modifying the loci.

Thus, in one aspect, the invention is directed to a method to produce a cell expressing an antibody from a genomic sequence of the cell comprising a modified immunoglobulin locus. The invention method uses Cre-mediated site-specific recombination and comprises:

(a) transfecting an antibody-producing cell with a first homology-targeting vector comprising: (i) a first lox site, and (ii) a targeting sequence homologous to a first DNA sequence adjacent to the region of the immunoglobulin locus of the genomic sequence which is to be converted to a modified region, so that the first lox site is inserted into the genomic sequence via site-specific homologous recombination with genomic DNA in vivo;

(b) transfecting said cell with a lox-targeting vector comprising: (i) a second lox site suitable for Cre-mediated recombination with the first lox site, and (ii) a modifying sequence to convert said region of the immunoglobulin locus to a modified region;

(c) interacting the lox sites with Cre, so that the modifying sequence inserts into the genomic sequence via Cre-mediated site-specific recombination of the lox sites, thereby converting the region of the immunoglobulin locus to the modified region; and (d) selecting a transfectant in which the region of the immunoglobulin locus is converted to the modified region and which produces the antibody molecule.

In one preferred embodiment of this method, the lox-targeting vector further comprises a selectable marker gene operably linked to control regions such that the marker gene is expressed in the cell. On interacting the lox sites with Cre, the marker gene inserts into the genomic sequence with the modifying sequence via Cre-mediated site-specific recombination of the lox sites. In this embodiment, selecting for a transfectant comprises selecting for expression of the marker gene.

A second preferred embodiment of the method of the invention further comprises an additional step before step (b), which additional step comprises transfecting the cell with a second homology-targeting vector comprising: (i) a third lox site suitable for Cre-mediated recombination with the first and second lox sites, (ii) a first selectable marker gene operably linked to control regions such that the first marker gene is expressed in the cell, and (iii) a targeting sequence homologous to a second DNA sequence adjacent to the region of the immunoglobulin locus of the genomic sequence which is to be converted. In this embodiment the gene which is to be converted is flanked by the first and second DNA sequences, and the third lox site and first marker gene are inserted into the genomic sequence via site-specific homologous recombination with genomic DNA in vivo.

Also in this second preferred embodiment the second targeting vector further comprises a second selectable marker gene operably linked to control regions such that the second marker gene is expressed in the cell. On interacting the lox sites with Cre, the second marker gene inserts into the genomic sequence with the modifying sequence via Cre-mediated site-specific recombination of appropriate lox sites. In this embodiment selecting for a transfectant comprises selecting for expression of the second marker gene. In a further variation of this embodiment of the method of the invention, on interacting the lox sites with Cre, after the modifying sequence and second marker gene insert into the genomic sequence, the first marker gene and the region to be converted are deleted by Cre-mediated site-specific recombination, and selecting for a transfectant further comprises selecting for a transfectant not expressing the first marker gene.

In some embodiments of the invention method, the modifying sequence comprises a regulatory nucleotide sequence which replaces all or a portion of the regulatory sequences of the immunoglobulin genes of the genomic sequence to provide modified expression of those immunoglobulin genes. In other embodiments, the modifying sequence comprises a nucleotide sequence that encodes a translation product to replace all or a portion of either the constant region or the variable region of an antibody molecule to form a modified antibody molecule. In some of the latter embodiments, the region of the immunoglobulin locus to be converted to a modified region comprises a constant region gene and the modifying sequence comprises a nucleotide sequence that encodes a translation product to replace all or a portion of the constant region of the antibody produced by said constant region gene with a modified constant region.

Sometimes the constant region gene of the genomic sequence is a human constant region gene and the modified constant region gene encodes a different human constant region. The modified constant region gene may comprise a light chain gene or a heavy chain gene. In various embodiments of the invention method to produce a cell expressing an antibody molecule with a modified constant region, the modified constant region gene comprises a sequence encoding an enzyme, toxin, hormone, growth factor, linker or mutant constant region with an altered heavy chain effector function.

In some embodiments of the invention method, the cell expressing an antibody molecule is a cell of a lymphoid cell line. This lymphoid cell line may be a murine hybridoma cell line producing either a murine, human or chimeric antibody. In some embodiments, the hybridoma cell line is producing a human antibody by expression of human immunoglobulin genes. In one particular embodiment the cell is a murine lymphoid cell producing a human antibody by expression of human immunoglobulin genes. In one variation of this embodiment, the constant region gene of the genomic sequence is a human constant region (C) gene of the mu class, i.e., a C, gene, and the modifying sequence comprises a human C gamma ($C_\gamma$) constant region gene.

In another aspect the invention is directed to a cell expressing an antibody from a genomic sequence of the cell comprising a modified immunoglobulin locus, where the cell is produced by the invention method above.

Another aspect of the invention is a method to produce a cell expressing an antibody molecule from a genomic sequence of the cell with a lox site adjacent to or integrated within a region of the immunoglobulin locus encoding the antibody molecule, for use in modifying that region using Cre-mediated site-specific recombination. This method comprises: (a) transfecting an antibody-producing cell with a first targeting vector comprising: (i) a first lox site, and (ii) a targeting sequence homologous to a first DNA sequence adjacent to the region of the immunoglobulin locus of the genomic sequence which is to be converted to a modified region, so that the first lox site is inserted into the genomic sequence via site-specific homologous recombination with genomic DNA in vivo. This method further comprises (b) selecting a transfectant with the lox site inserted into the genomic DNA adjacent to the region which is to be converted. This selection may be achieved using one or more selectable marker genes in a vector used to insert a lox site into the genomic sequence via site-specific homologous recombination with genomic DNA in vivo. Another facet of this aspect of the invention relates to a cell expressing an antibody molecule with a lox site adjacent to or integrated within a region of the immunoglobulin locus encoding an antibody molecule, where the cell is produced by the above method of the invention.

In yet another aspect the invention is directed to an embryonic stem cell of a non-primate mammal comprising a genome comprising a transgenic non-primate mammal comprising a genome comprising: at least a functional portion of a human heavy chain immunoglobulin locus or at least a functional portion of a human light chain immunoglobulin locus. In the genome of this stem cell, a lox site is adjacent to or integrated within a region of said human heavy chain or light chain immunoglobulin locus. In a preferred embodiment, this stem cell is a murine stem cell.

A related aspect of the invention is a transgenic non-primate mammal comprising a genome comprising: at least a functional portion of a human heavy chain immunoglobulin locus or at least a functional portion of a human light chain immunoglobulin locus. In the genome of this stem cell, a lox site is adjacent to or integrated within a region of said human heavy chain or light chain immunoglobulin locus. In a preferred embodiment, this transgenic mammal is murine.

Other aspects of the invention are described below.

MODES OF CARRYING OUT THE INVENTION

Definitions

Figure 1:
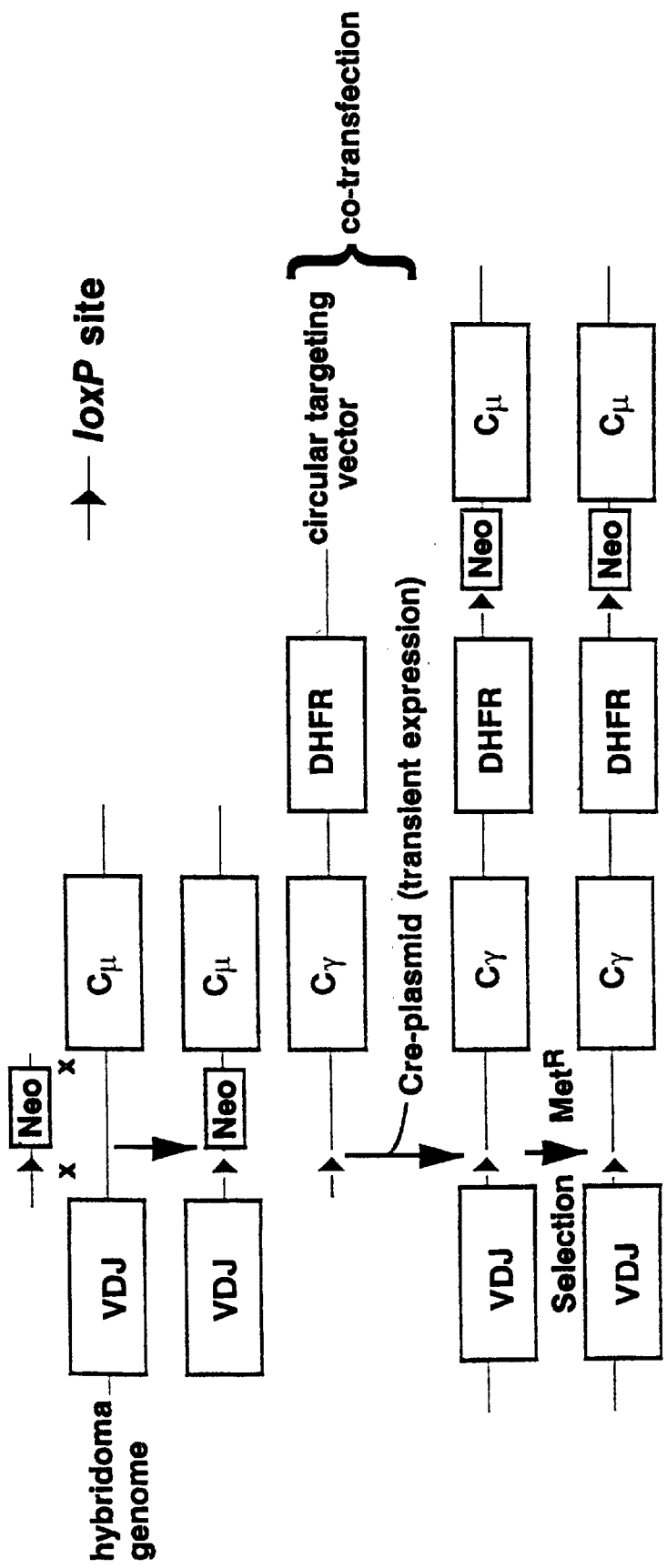
FIG. 1 represents a schematic diagram of one embodiment (Scheme A) of the invention method to produce a cell expressing a human antibody molecule with a modified constant region using Cre-mediated site-specific recombination. This scheme requires insertion of only a single lox site adjacent to the constant region gene to be modified.

The following terms, as used herein, whether in the singular or plural, shall have the meanings indicated:

Immunoglobulin locus: a nucleotide sequence that encodes all or a portion of either the constant region or variable region of an antibody molecule or all or a portion of a regulatory nucleotide sequence that controls expression of an antibody molecule. Immunoglobulin loci for heavy chains may include but are not limited to all or a portion of the V, D, J, and switch regions (including intervening sequences called introns) and flanking sequences associated with or adjacent to the particular heavy chain constant region gene expressed by the antibody-producing cell to be transfected and may include regions located within or downstream of the constant region (including introns). Immunoglobulin loci for light chains may include but are not limited to the V and J regions, their upstream flanking sequences, and intervening sequences (introns), associated with or adjacent to the light chain constant region gene expressed by the antibody-producing cell to be transfected and may include regions located within or downstream of the constant region (including introns). Immunoglobulin loci for heavy chain variable regions may include but are not limited to all or a portion of the V, D, and J regions (including introns) and flanking sequences associated with or adjacent to the particular variable region gene expressed by the antibody-producing cell to be transfected. Immunoglobulin loci for light chain variable regions may include but are not limited to the V and J region (including introns) and flanking sequences associated with or adjacent to the light chain variable region gene expressed by the antibody-producing cell to be transfected.

Modified Antibody: an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the modified antibody, e.g., an enzyme, toxin, hormone, growth factor, drug, and the like; or (b) the variable region, or a portion thereof, is altered, replaced or exchanged with a variable region having a different or altered antigen specificity.

Modifying Sequence: a nucleotide sequence that encodes (a) a translation product to modify or replace all or a portion of either the constant region or variable region of an antibody molecule to form a modified antibody molecule, or (b) one or more regulatory nucleotide sequences to modify or replace all or a portion of the regulatory sequences of an immunoglobulin locus sequence to provide modified expression of that immunoglobulin locus sequence. This regulatory sequence may include, for instance, a promoter, enhancer, an intron, a switch sequence, a ribosome binding site, and the like, and may be in addition to or instead of a sequence that encodes a translation product to replace a region of an antibody molecule. Suitable regulatory nucleotide sequences are known in the art. The regulatory nucleotide sequence which is employed with a selected antibody-producing cell is not critical to the method of the invention. Preferred regulatory sequences for modification of expression of immunoglobulin sequences in antibody-producing cells include a mouse heavy chain enhancer sequence, mouse kappa (κ) chain enhancer sequence, or a promoter derived from Moloney murine leukemia virus, Rous sarcoma virus or spleen focus forming virus.

Modifying sequences are inserted into recombinant DNA targeting vectors of the invention which are used to transfect antibody-producing or embryonic stem cells. For the modification of all or a portion of a constant region of an antibody, modifying sequences of the invention may include, but are not limited to an immunoglobulin constant region having a particular effector function, class and/or origin (e.g., IgG, IgA, IgM, IgD, or IgE constant regions of human immunoglobulins or any other species) or a portion of a constant region which modifies the activity or properties of the constant region of the immunoglobulin; as well as genes which encode other molecules that confer some new function to a modified antibody molecule, e.g., an enzyme, toxin, a biologically active peptide, growth factor, inhibitor, conjugatable peptide linker, and the like. For the modification of all or a portion of a variable region of an antibody, modifying sequences of the invention may include, but are not limited to immunoglobulin variable regions that encode a different variable region having a different antigen affinity or specificity, or a portion of a variable region which modifies the activity or properties of the variable region of the immunoglobulin so that the resulting modified antibody has a greater affinity or higher degree of specificity for the antigen.

The modifying sequence chosen depends, in part, upon the use intended for the modified antibody molecule expressed. For example, if therapeutic use in humans is intended, then the modifying sequence could encode a human constant region, preferably of a class having a desired effector function for the therapeutic use in mind, such as a toxin for killing targeted tumor cells. If an improvement or alteration in the existing effector function of the antibody is desired, a portion of the constant region may be replaced with a sequence that confers such improved or altered effector function to the resulting modified antibody molecule. For instance, where it is desired to reduce the rate of clearance of the antibody from the circulatory system, such as with antibodies used for imaging or delivery of cytotoxic drugs to a target cell, a portion of a human $\gamma_2$ heavy chain region may be replaced with a region from a $\gamma_2$ heavy chain region containing a mutation which eliminates binding of the $\gamma_2$ heavy chain to Fc receptors.

If targeted delivery of an enzyme, toxin, drug, hormone or growth factor in vivo is desired, a modifying sequence encoding the enzyme, toxin, drug, hormone or growth factor or an appropriate linker for conjugation to such is used. If the modified antibodies are to be used in diagnostic assays, for example where labeled antibodies are utilized, a modifying sequence encoding an enzyme or its substrate could be used. Such enzyme/substrate systems include, but are not limited to those which produce a colored product when reacted; for example, beta-galactosidase, alkaline phosphatase, horseradish peroxidase, and the like. The resulting modified antibodies may be used as labeled antibodies in the procedures intended with or without further modification, e.g., the chemical attachment of enzymes, drugs, toxins, hormones, growth factors, and the like.

The modifying sequence used to convert antibody variable regions may comprise all or a portion of the coding sequence for a variable region of an antibody molecule that recognizes a desired antigen. These may encode antigen binding regions that recognize related or completely unrelated antigens. If an improvement or alteration in antigen binding or specificity is desired, a portion of the variable region may be replaced with a sequence that confers such improved or altered binding or specificity to the resulting modified antibody molecule. The invention method also is useful to construct cells that produce bi-specific antibodies, i.e., antibodies which contain two different variable regions, by modifying cells to contain two different variable regions in the light and/or heavy chain genes. In this context, if a wildtype and incompatible mutant lox site are integrated into the same genome, a particular modifying sequence can be inserted selectively into either of these sites by using a vector comprising a site compatible with the desired integrated site, as described, for instance, by Johnson et al., in PCT Publication WO93/19172.

Cre: The enzyme expression product of the cre gene which is a recombinase that effects site-specific recombination of DNA at lox sites (see definition below). One cre gene can be isolated from bacteriophage P1 by methods known in the art, for instance, as disclosed by Abremski et al., *Cell*, 32:1301–1311 (1983), the entire disclosure of which is incorporated herein by reference.

Lox Site: a nucleotide sequence at which the gene product of the cre gene, referred to herein as "Cre," can catalyze a site-specific recombination. A LoxP site is a 34 base pair nucleotide sequence which can be isolated from bacteriophage P1 by methods known in the art. One method for isolating a LoxP site from bacteriophage P1 is disclosed by Hoess et al., *Proc. Natl. Acad. Sci. USA*, 79:3398 (1982), the entire disclosure of which is hereby incorporated herein by reference. The LoxP site consists of two 13 base pair inverted repeats separated by an 8 base pair spacer region. The nucleotide sequences of the insert repeats and the spacer region of LoxP are as follows.

ATAACTTCGTATA ATGTATGC TATACGAAGTTAT

Other suitable lox sites include LoxB, LoxL and LoxR sites which are nucleotide sequences isolated from *E. coli*. These sequences are disclosed and described by Hoess et al., *Proc. Natl. Acad. Sci. USA* 79:3398 (1982), the entire disclosure of which is hereby incorporated herein by reference. Preferably, the lox site is LoxP or LoxC2. The nucleotide sequences of the insert repeats and the spacer region of LoxC2 are as follows.

ACAACTTCGTATA ATGTATGC TATACGAAGTTAT

Johnson et al., in PCT Publication WO93/19172, the entire disclosure of which is hereby incorporated herein by reference, describes phage vectors in which the VH genes are flanked by two loxP sites, one of which is a mutant loxP site (loxP 511) with the G at the seventh position in the spacer region of loxP replaced with an A, which prevents recombination within the vector from merely excising the VH genes. However, two loxP 511 sites can recombine via Cre-mediated recombination and, therefore, can be recombined selectively in the presence of one or more wildtype lox sites. The nucleotide sequences of the insert repeats and the spacer region of loxP 511 as follows.

ATAACTTCGTATA ATGTATAC TATACGAAGTTAT

Lox sites can also be produced by a variety of synthetic techniques which are known in the art. For example, synthetic techniques for producing lox sites are disclosed by Ito et al., *Nuc. Acid Res.*, 10:1755 (1982) and Ogilvie et al., *Science*, 214:270 (1981), the entire disclosures of which are hereby incorporated herein by reference.

Cre-Mediated Site-Specific Recombination: a process of recombination between two compatible lox sites including any of the following three events:

1. deletion of a preselected DNA segment flanked by lox sites,
2. inversion of the nucleotide sequence of a preselected DNA segment flanked by lox sites, and
3. reciprocal exchange of DNA segments proximate to lox sites located on different DNA molecules. It is to be understood that this reciprocal exchange of DNA segments results in an integration event if one or both of the DNA molecules are circular. Thus, where a lox-targeting vector is used according to the invention to insert (i.e., integrate) a modifying sequence into the genome of an antibody-producing cell having a single lox site suitable for recombination with a lox site in the vector, it is to be understood that the lox-targeting vector in such a case is comprised of a circular DNA molecule. A linear DNA segment flanked by lox sites also may be inserted into a DNA molecule comprising a single lox site by recombination between the flanking lox sites to form a circular segment followed by integration of that circle into the DNA molecule comprising a single lox site.

Targeting sequence: a sequence homologous to DNA sequences in the genome of a cell that flank or occur adjacent to the region of an immunoglobulin locus to be converted. The flanking or adjacent sequence may be within the locus itself or upstream or downstream of coding sequences in the genome of an antibody-producing cell. Targeting sequences are inserted into recombinant DNA vectors which are used to transfect antibody-producing cells such that sequences to be inserted into the cell genome, such as the sequence of a lox site, are flanked by the targeting sequences of the vector.

For antibody-producing or embryonic stem cells, targeting sequences for heavy chain recombinations that direct replacement of or insertion within all or a portion of the constant region may include but are not limited to all or a portion of the V, D, J, and switch region (including intervening sequences called introns) and flanking sequences associated with or adjacent to the particular heavy chain constant region gene expressed by the antibody-producing cell to be transfected and may include regions located within or downstream of the constant region (including introns). Targeting sequences for light chain recombinations that direct replacement of or insertion within all or a portion of the constant region may include but are not limited to the V and J regions, their upstream flanking sequences, and intervening sequences (introns), associated with or adjacent to the light chain constant region gene expressed by the antibody-producing cell to be transfected and may include regions located within or downstream of the constant region (including introns). Targeting sequences for heavy chain recombinations that direct replacement of or insertion within all or a portion of the variable region may include but are not limited to all or a portion of the V, D, and J regions (including introns) and flanking sequences associated with or adjacent to the particular variable region gene expressed by the antibody-producing cell to be transfected. Targeting sequences for light chain recombinations that direct replacement of or insertion within all or a portion of the variable region may include but are not limited to the V and J region (including introns) and flanking sequences associated with or adjacent to the light chain variable region gene expressed by the antibody-producing cell to be transfected.

Targeting sequences for homology-targeting vectors of the present invention are usually further selected from those described above such that insertion of a lox site into a genomic sequence via site-specific homologous recombination of an associated targeting sequence with genomic DNA in vivo does not modify an amino acid sequence of the antibody molecule which is expressed by the transfected cell. This approach maintains the proper transcription and translation of the immunoglobulin genes which produce the desired antibody after insertion of lox sites (and, optionally, any additional sequence such as a selectable marker gene). However, in some cases it is possible to insert a lox site and other sequences into an immunoglobulin locus sequence such that an amino acid sequence of the antibody molecule is altered by the insertion, but the antibody still retains sufficient functionality for the desired purpose. For instance, Waterhouse et al., *Nucleic Acids Res* (1993) 21:2265–2266, the entire disclosure of which is hereby incorporated herein by reference, describes DNA sequences encoding an IgM or IgG polypeptide chain linked to a phage protein via an amino acid sequence encoded by a 34 base pair lox site. This construct produces an antibody variable region fused to the phage protein in such a way that the phage particle displays functional antibody binding sites. Functional antibody regions may be linked to other polypeptides, such as a toxin, using these or similar constructs including DNA sequences encoding an IgM or IgG polypeptide chain linked to the polypeptide via an amino acid sequence encoded by a lox site.

Vector: includes plasmids and viruses and any DNA or RNA molecule, whether self-replicating or not, which can be used to transform or transfect an antibody-producing cell.

Homology-Targeting Vector: a recombinant DNA or RNA vector comprising a targeting sequence and any other sequence, particularly a lox site and optionally a selectable marker gene, which is used to modify immunoglobulin loci using homology-mediated site-specific recombination in antibody-producing cells or embryonic stem cells transfected with the homology-targeting vector. Homology-targeting vectors are typically transfected into antibody-producing cells in the form of linear DNA molecules to enhance the desired homologous recombination event.

Lox-Targeting Vector: a recombinant DNA or RNA vector comprising a lox site and any other sequence, particularly a modifying sequence and optionally a selectable marker gene, which is used to modify immunoglobulin loci using Cre-mediated site-specific recombination in antibody-producing cells. The lox site of the lox-targeting vector is suitable for Cre-mediated recombination with another lox site which has been inserted into a genomic sequence of the antibody-producing or embryonic stem cell (via a homology-targeting vector), adjacent to a region of the immunoglobulin loci which is to be modified by the modifying sequence. Integration of a modifying sequence into a single lox site in a region of the immunoglobulin loci in the genome of the antibody-producing or embryonic stem cell results in modification of that region by addition of the modifying sequence. Integration of a modifying sequence into a genome comprising two lox sites flanking a region to be modified results in replacement of that region with the modifying sequence.

Antibody-Producing Cells: The homology-targeting and lox-targeting vectors are used to transfect cells that contain sequence(s) homologous to the targeting sequence of the vector and that are capable of producing immunoglobulin molecules having (a) a desired antigen specificity or affinity; (b) a desired constant region; or (c) another desired quality such as high secretion levels, large scale culture adaptability, and the like. Such cells include, but are not limited to, cell lines derived from hybridomas which produce a monoclonal antibody having a desirable specificity, affinity or effector function, as well as hybridoma cells which themselves have sustained mutations which prevent expression of heavy and/or light chains of immunoglobulin.

In certain preferred embodiments of the invention methods, the antibody-producing cells are hybridomas derived from B-cells of mice engineered with human immunoglobulin heavy and light chain genes, as described for instance by Kucherlapati et al., in PCT Publication WO91/10741 (published Jul. 25, 1991) and in PCT Publication WO 94/02602 (published Feb. 3, 1994). Such mice produce human antibodies in response to immunization with any antigen normally recognized by the mouse immune system, including human antigens; and B-cells from these mice can be used to make hybridomas producing human monoclonal antibodies via conventional hybridoma production methods. In one particular embodiment using hybridomas from such transgenic mice, the genomic sequence comprising the human immunoglobulin loci in the transgenic mouse further comprises a lox site adjacent to or inserted in a region of the immunoglobulin locus which is to be modified in the hybridomas by the invention method. This lox site is inserted adjacent to or with the human immunoglobulin loci prior to their insertion into the genome of the murine embryonic stem cells by incorporation into whatever vector is used to insert the human immunoglobulin loci into the genome of the embryonic stem cells from which transgenic mice, as described, for instance, by Kucherlapati et al., supra. Conventional recombinant DNA methods are used to incorporate the lox site into this vector, adjacent to or inserted in a region of the immunoglobulin locus which ultimately is to be modified by the invention method in an antibody producing cell obtained from the transgenic mouse.

In addition, antibody-producing cells suitable for practice of the invention methods for engineering of antibodies include host cells of both prokaryotic and eukaryotic organisms disclosed by Cabilly, et al. in U.S. Pat. No. 4,816,567, the entire disclosure of which is hereby incorporated herein by reference.

The following abbreviations shall have the meanings shown below:

DHFR: dihydrofolate reductase
gpt: guanosine phosphoryl transferase gene
Neo: neomycin resistance gene
Hyg: hygromycin resistance gene Invention methods for modifying immunoglobulin loci The invention relates to the novel use of Cre-mediated site-specific recombination for engineering immunoglobulin loci, such as for class-switching of antibody genes in antibody-producing lymphoid cells in situ whereby the constant region of an antibody gene is replaced with a constant region of another class, thereby producing an antibody with a changed or "switched" isotype. The resulting cells can be used for large scale production of the modified antibodies. More particularly, the present invention provides methods to produce a cell expressing a modified antibody molecule with a modified constant region, or a lymphoid cell line expressing a modified antibody molecule, using Cre-mediated site-specific recombination to target gene modifications to desired locations in the genomic sequence of the immunoglobulin loci of an antibody-producing cell.

In the methods of the invention, DNA sequences comprising one or more lox sites are first introduced into the genome of the antibody-producing cell by homologous recombination. Insertion of the lox site(s) is adjacent to a region of the immunoglobulin loci of the antibody-producing cell which is to be converted to a modified region. The cells containing a genome with one or more integrated lox sites are then transfected with a DNA molecule comprising: (a) a lox site suitable for Cre-mediated recombination with an integrated lox site, and (b) a modifying sequence. The genomic and vector lox sites are then interacted with the Cre recombinase (typically, by transient expression of the recombinase from a plasmid), thereby producing recombination between the lox sites so that the modifying sequence inserts into the genomic sequence via Cre-mediated site-specific recombination of the lox sites, thereby converting the desired portion of the genomic sequence to a modified portion.

In this method, interacting the lox sites with Cre is typically performed by transient expression of the recombinase from a plasmid. Transient interaction with Cre is particularly preferred where the object is to produce a limited number of recombination events resulting in constructs containing multiple lox sites because extensive Cre-mediated recombination would tend to produce undesired deletions from such constructs.

Using the method of the invention, the amino acid sequence of an antibody molecule can be modified by transfection of an antibody-producing cell with an appropriate "homology-targeting vector" and "lox-targeting vector" and interaction of the lox sites with the Cre recombinase. In one embodiment of the invention, a cell line that comprises immunoglobulin loci encoding a desired antigen specificity or affinity is transfected with a lox-targeting vector of the invention which comprises a recombinant DNA molecule that encodes a lox site and a "modifying sequence." The modifying sequence encodes the desired molecule which is to replace all or a portion of the constant region of the antibody molecule expressed by the antibody-producing cell. Examples of modifying sequences for this embodiment are described above.

In this embodiment a lox site is integrated into the genomic DNA of the antibody-producing cell using a homology-targeting vector in which the "targeting sequence" is homologous to DNA sequences found in the chromosome within or adjacent to the mature gene coding sequence for the constant region of the immunoglobulin encoded by the cell line to be transfected. After transfection, homologous recombination within the antibody-producing cell will occur; some of these recombination events will lead to the integration of the lox site into the genomic DNA of the antibody-producing cell at the desired location. Subsequent Cre-mediated site-specific recombination between a lox-targeting vector and one or more integrated lox sites results in replacement of all or a portion of the constant region of the immunoglobulin locus with the modifying sequence of the lox-targeting vector, and, therefore, the expression of modified antibody molecules by the transfected cells. The extent of replacement of the constant region gene (i.e., all or a portion) depends, of course, on the location of the integrated lox site(s) within the immunoglobulin locus of the cell and on the nature of the modifying sequence in the lox-targeting vector.

In another aspect of the invention, a lymphoid cell line which comprises an immunoglobulin locus encoding a desired constant region is transfected with a homology-targeting vector to insert a lox site adjacent to a variable region in the genome which is to be modified, followed by transfection with a lox-targeting vector containing a modifying sequence encoding all or a portion of a variable region having a desired antigen specificity or affinity. After transfection and interacting the lox sites with Cre, Cre-mediated recombination within the lymphoid cell line will occur; some of these recombination events will lead to the replacement of all or a portion of the variable region of the immunoglobulin locus with the modifying sequence and, therefore, to the expression of modified antibody molecules by the transfected cells.

Once the transfectant that expresses the modified antibody is identified, the practice of the invention involves culturing the transfectant and isolating the modified antibody molecules from the cell culture supernatant using techniques well known in the art for isolating monoclonal antibodies. Alternatively, the transfected cells may be cultured in ascites fluid in animals and harvested using well known techniques for isolating monoclonal antibodies.

All of the modifications in immunoglobulin loci of antibody-producing cells described herein may be made by first introducing a lox site into the genome of an antibody-producing cell by transfecting that antibody-producing cell with a homology-targeting vector of the invention. However, antibody-producing cells with genomes comprising lox sites suitable for use in the invention also may be produced by making hybridomas of B-cells from transgenic mice which contain the lox site integrated into germ line DNA. These mice are produced by methods such as those described by Kucherlapati et al., in PCT Publication WO91/10741 (published Jul. 25, 1991) and in PCT Publication WO94/02602 (published Feb. 3, 1994), the entire disclosures of which are hereby incorporated herein by reference. Such transgenic mice also may be produced by other methods for production of transgenic mice which are known in the art. Generally, the embryonic stem cells used to produce the transgenic mice are transformed by any convenient method with a construct containing human immunoglobulin heavy and light chain genes and further containing a lox site adjacent to or integrated within the region of the human immunoglobulin loci (e.g., a heavy chain gene) which ultimately is to be modified in an antibody-producing cell obtained from these transgenic mice. Antibody-producing cells are obtained from the transgenic mice, for instance, by conventional hybridoma production methods.

Use of homology-targeting vectors to insert lox sites

In the methods of the invention DNA sequences comprising lox sites are first introduced into the genome of the antibody-producing or embryonic stem cell by homology-targeted site-specific recombination using known methods for insertion of genes via homologous recombination, as described, for instance, by Fell et al. in U.S. Pat. No. 5,202,238, the entire disclosure of which is hereby incorporated herein by reference. In the invention method the lox site(s) are inserted adjacent to a region of the immunoglobulin loci of the genomic sequence of the antibody-producing or embryonic stem cell which ultimately is to be converted to a modified region.

The targeting vectors (i.e., homology-targeting or lox-targeting vectors) of the invention comprise recombinant DNA vectors including, but not limited to, plasmids, phages, phagemids, cosmids, viruses and the like, which contain the lox sites and/or modifying sequences and/or targeting sequences. As described in more detail above, the modifying sequence may comprise any of a number of regulatory sequences or genes that encode a desired structural product whereas the targeting sequence may vary depending upon the type of antibody molecule being converted and the cell-type being transfected. The targeting vectors of the invention may contain additional genes which encode selectable markers including but not limited to enzymes which confer drug resistance to assist in the screening and selection of transfectants. Alternatively the vectors of the invention may be cotransfected with such markers.

Other sequences which may enhance the occurrence of recombinational events may be included in homology-targeting vectors as well. Such genes may include but are not limited to genes for either eukaryotic or procaryotic recombination enzymes such as Rec A, topoisomerase, Rec 1 or other DNA sequences which enhance recombination such as Chi. Furthermore, sequences which enhance transcription of chimeric genes produced by homologous recombination may also be included in the vectors of the invention; such sequences include, but are not limited to, inducible elements such as the metallothionine promoter (Brinster et al., 1982, *Nature* 296:39–42). Various proteins, such as those encoded by the aforementioned genes may also be transfected in order to increase recombination frequencies.

For modification of antibodies, the composition of the targeting sequence may vary depending upon whether the homology-targeting vector is to be used to replace all or a portion of either the variable or constant region genes of light chains or heavy chains and, further, upon the species of the host cell to be transfected. More specifically, targeting sequences are homologous to sequences which are adjacent to or which flank the coding region for the constant or variable region, or the portion thereof, to be replaced or altered.

For example, in a vertebrate chromosome, mature heavy chain genes are comprised, at their 5' termini, of the VDJ regions; i.e., the variable region (V), diversity region (D), and joining region (J) followed by any remaining J regions which are not expressed (the number of J regions varies with the species), and intronic sequences. The central and 3' portion of the gene consists of the constant region exons (flanked and interspersed with intronic and untranslated sequences) which may be one of various classes (e.g., mu, delta, gamma, epsilon, alpha) each of which is associated with its own adjacent switch region. Thus, the targeting sequence used to target insertion of a lox site by homologous recombination in the heavy chain gene of an antibody-producing cell may comprise a region that is homologous to any portion of the antibody gene, depending on the desired location for insertion of the lox site. For example, the targeting sequence for inserting a lox site to direct replacement of a heavy chain constant region may comprise sequences homologous to sequences spanning any region up to and including or excluding the switch region commencing with V, D or J and would be positioned accordingly in the construction of the targeting vector; e.g., at a location 5' to the coding region of the modifying sequence. The actual targeting sequence that could be used may vary depending upon the species of the target host cell and the class of antibody expressed by the target host cell.

In some applications the lox site is inserted into the genomic sequence by homologous recombination without modifying an amino acid sequence of the antibody which ultimately is to be modified using Cre-mediated site-specific recombination. In such cases involving the mature heavy chain genes of an antibody-producing cell, a lox site may be inserted into any suitably located non-translated portion of those genes, such as: at their 5' termini, any remaining J regions which are not expressed and intronic sequences; and in the central and 3' portion of the gene, the constant region intronic and untranslated sequences, provided that such insertion does not disrupt expression of the desired heavy chain molecule.

By contrast to the arrangement of heavy chain antibody genes in a chromosome, the mature light chain genes are composed of a VJ region at their 5' termini, intronic sequences, and a single constant region exon. Thus, the targeting sequence used to insert a lox site by homologous recombination in the light chain gene of an antibody-producing host cell may comprise a region that is homologous to any portion of the gene, depending on the desired alteration. For example, the targeting sequence for directing the replacement of a light chain constant region may be homologous to sequences spanning all or portions of the appropriate V and J through intronic sequences preceding the coding region for the constant region of the light chain. Such targeting sequences would be appropriately positioned in the homology-targeted plasmid; e.g., at a location 5' to the lox site, such that the lox site is integrated into a non-translated sequence of the light chain genes, such as in an intronic sequences preceding the coding region for the constant region of the light chain. Once again, the actual nucleotide sequence of the targeting sequence may vary with respect to the animal species of the target host antibody-producing cell.

In a similar fashion, targeting sequences for directing insertion of lox sites for Cre-mediated replacement of heavy or light chain variable regions of antibodies may comprise sequences homologous to all or portions of the appropriate regions that flank the variable region. In any case, targeting sequences may also include coding region sequences flanking an area within an exon where only a portion of the variable or constant region is to be replaced so that the protein expressed is altered in a desired fashion.

Use of Cre-mediated site-specific recombination

In the methods of antibody engineering of the invention, cells containing a genome with one or more integrated lox sites are transfected with a lox-targeting vector, i.e., typically a DNA molecule comprising a lox site suitable for Cre-mediated site-specific recombination with an integrated lox site, and the lox sites are then interacted with the Cre recombinase, thereby producing recombination at the lox sites. The location and orientation of the lox sites determines the nature of the recombination, as described herein and more fully by Sauer et al. in U.S. Pat. No. 4,959,317, the entire disclosure of which is hereby incorporated herein by reference.

In addition to the lox site, targeting sequence and the modifying sequence, the various targeting vectors of the invention may encode a selectable marker which assists in the screening and selection of antibody-producing cells that have been successfully transformed. Suitable selectable marker genes include drug resistance genes, such as hyg, gpt, neo and DHFR (as defined above under "abbreviations") and the like.

Methods for introducing a DNA sequence (e.g., a lox-targeting vector or a homology-targeting vector) into antibody-producing cells are known in the art. These methods typically include the use of a DNA vector to introduce the sequence into the DNA of a single or limited number of antibody-producing cells and then growing such cell or cells to generate a suitable population of cells. Preferably, the DNA sequences are introduced by a plasmid capable of transforming a selected eukaryotic cell while carrying a DNA sequence. The particular vector which is employed to introduce the DNA sequence into a selected antibody-producing cell is not critical.

In a preferred embodiment, DNA sequences are introduced into mammalian cells according to the $CaPO_4$ transfer procedure described by Graham and van der Eb, *Virology*, 52:456–467 (1973), the entire disclosure of which is hereby incorporated herein by reference. Transfection of lymphoid cell lines in particular may be accomplished by any of a number of methods known to those skilled in the art, including, but not limited to calcium phosphate precipitation, electroporation, microinjection, liposome fusion, RBC ghost fusion, protoplast fusion, and the like. For homologous recombination the homology-targeting vector may be linearized by cleavage with a restriction enzyme within the targeting sequence prior to transfection in order to increase the probability of homologous recombination in the transfected cell.

In the present methods, Cre is introduced to interact with the lox sites, thereby producing the site-specific Cre-mediated recombination. In one embodiment, Cre is introduced into the cells directly by microinjection. In a preferred embodiment, the cre gene is introduced into the antibody-producing cell under the control of a regulatory nucleotide sequence. Suitable regulatory nucleotide sequences are known in the art. The regulatory nucleotide sequence which is employed with a selected antibody-producing cell is not critical to the method of the invention. A partial list of suitable regulatory nucleotide sequences for mammalian cells includes the long terminal repeat of Moloney sarcoma virus described by Blochlinger and Diggelmann, *Mol. Cell Bio.*, 4:2929–2931 (1984); the mouse metallothionein-1 (MT-1) promoter described by Pavlakis and Hamer, *Proc. Natl. Acad. Sci. USA*, 80:397–401 (1983); the long terminal repeat of Rous sarcoma virus described by Gorman et al., *Proc. Natl. Acad. Sci. USA*, 79:6777–6781 (1982); and the early region promoter of SV40 described by Southern and Berg, *J. Mol. Appl. Genet.*, 1:327–341 (1982). Sauer et al., in U.S. Pat. No. 4,959,317, describes a plasmid for expression of Cre in mammalian cells, plasmid PBS31, containing a cre gene upstream from a MT-1 promoter. Activation of the MT-1 promoter with $CdCl_2$ effects expression of the cre gene in cells transfected with this vector.

Since the lox site is an asymmetrical nucleotide sequence, two lox sites on the same DNA molecule can have the same or opposite orientations with respect to each other. Recombinations between lox sites in the same orientation result in a deletion of the DNA segment located between the two lox sites and a connection between the resulting ends of the original DNA molecule. The deleted DNA segment forms a circular molecule of DNA. The original DNA molecule and the resulting circular molecule each contains a single lox site. Recombination between lox sites in opposite orientations on the same DNA molecule result in an inversion of the nucleotide sequence of the DNA segment located between the two lox sites. In addition, reciprocal exchange of DNA segments proximate to lox sites located on two different DNA molecules can occur resulting in two new recombinant DNA molecules. All of these recombination events are catalyzed by the gene product of the cre gene.

Screening and Selection of Recombinants

The ultimate test for successful targeted gene modification is the production of modified antibodies by the cell. The detection of transfectants with properly integrated vector sequences can be accomplished in a number of ways, depending upon the nature of the integrated sequences. If the targeting vector contains a selectable marker, the initial screening of transfected cells is to select those which express the marker. For example, when using a drug resistance gene, those transfectants which grow in the selection media containing the otherwise lethal drug can be identified in the initial screening. A second screening is then required to identify those transfectants which have integrated a lox site of a homology-targeting vector or a modifying sequence of a lox-targeting vector, where the latter cell will express the modified antibody.

The protocol for the second screening depends upon the nature of the inserted sequences. For example, integrated lox sites are detected by treatment of isolated cell DNA with Cre in vitro followed by Southern blot analysis using appropriate restriction enzymes, as described, for instance, by Sauer et al., U.S. Pat. No. 4,959,317. Alternatively, cells transfected with a homology-targeting vector are tested for insertion of a lox site by polymerase chain reaction (PCR) amplification of the specific gene region which is supposed to contain the integrated lox site and examination of the amplified DNA for the presence of a lox site (e.g., by size or sequence), according to conventional methods. In yet another alternative approach, verification of insertion of the lox site is performed indirectly, by testing for efficiency of correct integration of a modifying sequence carried by a lox-targeting vector of the invention.

The expression of a modifying sequence that encodes the constant region of a different antibody class or species is detected, for instance, by an immunoassay using antibodies specific for the particular immunoglobulin class and/or species. Alternatively, a bioassay is performed to test for a particular effector function conferred by the modifying sequence. The expression of a modifying sequence which encodes a biologically active molecule such as an enzyme, toxin, growth factor, or other peptide is assayed for the particular biological activity; for example, the transfected cell products are tested using the appropriate enzyme substrate, or target for the toxin, growth factor, hormone, and the like. Alternatively, these modifying sequence products are assayed immunologically using antibodies which are specific for the modifying sequence product.

According to a modification of a method disclosed by Fell et al. in U.S. Pat. No. 5,202,238, antibody-producing cells with an integrated lox site are transfected with a lox-targeting vector comprising human constant region sequences, as described supra, and then cultured in a single flask of selective media. After a period of time sufficient to allow selection to occur (in most cases, about 2 weeks) the surviving cells are then treated with antibody that is specific for whatever immunoglobulin constant region was originally produced by the antibody-producing cell conjugated to a toxin, such as ricin. Cells which are not successfully transfected continue to express antibody which contains murine constant region sequences, and are killed by the toxin conjugated to the anti-murine immunoglobulin antibody. Cells expressing modified antibodies which contain the desired human constant region sequences would survive, and are subsequently cultured in soft agar and further identified by an overlay of anti-human immunoglobulin antibody.

The transfectants which express a modifying sequence also are tested for appropriate antigen or ligand recognition via any conventional immunological binding methods, for instance, as disclosed by Fell et al., supra or Capon et al., supra. If the cell in which antibody genes are to be modified originally is incapable of producing functional antibody (for example, because it is capable of producing only light chain), after transfection with any targeting vector of the invention, useful transfectants are identified by assays known in the art which identify functional antibody, including, but not limited to, CDC, ADCC, or immunoprecipitation reactions.

The following examples are intended to illustrate, but not to limit, the invention.

EXAMPLE 1

"Class-Switching" of Human Antibodies Produced in Murine Hybridoma Cells

FIG. 1 represents a schematic diagram of one embodiment (Scheme A) of the invention method to produce a cell expressing a human antibody molecule with a modified constant region using Cre-mediated site-specific recombination. The cell to be modified is from a lymphoid cell line (hybridoma) with a genome containing a human constant region gene which is to be converted to a modified constant region. Such cell lines may be generated, for instance, by transformation of murine hybridomas with vectors containing human constant region genes which are integrated using homologous recombination methods such as described by Fell, et al., supra. Such cell lines also are described by Kucherlapati et al., in PCT Publication WO91/10741 (published Jul. 25, 1991) which discloses production of antigen-specific human monoclonal antibodies from mice engineered with human immunoglobulin heavy and light chain genes. B-cells from these mice are used to make hybridomas producing human monoclonal antibodies via conventional hybridoma production methods.

The invention method in Scheme A requires integration of only a single lox site adjacent to the constant region gene to be modified. In this scheme, a first lox site is integrated adjacent to the constant region gene (human $C_\mu$) which is to be converted to a modified constant region (human $C_\gamma$), via site-specific homologous recombination with genomic DNA. A vector (comprised of a circular DNA) comprising a second lox site and a selectable marker gene (DHFR) is then transfected into the cells, and the lox sites are transiently interacted with Cre. Cre is provided by cotransfection of a vector which transiently expresses a cre gene, as described above. Cre-mediated site-specific recombination of the lox site in the genome with the lox site on the circular vector results in insertion into the genome of the modifying sequence ($C_\gamma$) with the selectable marker gene (DHFR). The desired transfectants, which have two lox sites flanking the DHFR and $C_\gamma$ genes, are stable in the absence of further Cre expression and are obtained by selecting for expression of the DHFR marker gene (i.e. resistance to the drug methotrexate indicated as "$Met^R$" in FIG. 1). Verification of the desired modifications of the immunoglobulin loci after each transfection and selection step is provided by conventional genetic analyses, such as by PCR amplification, as described above.

Figure 2:
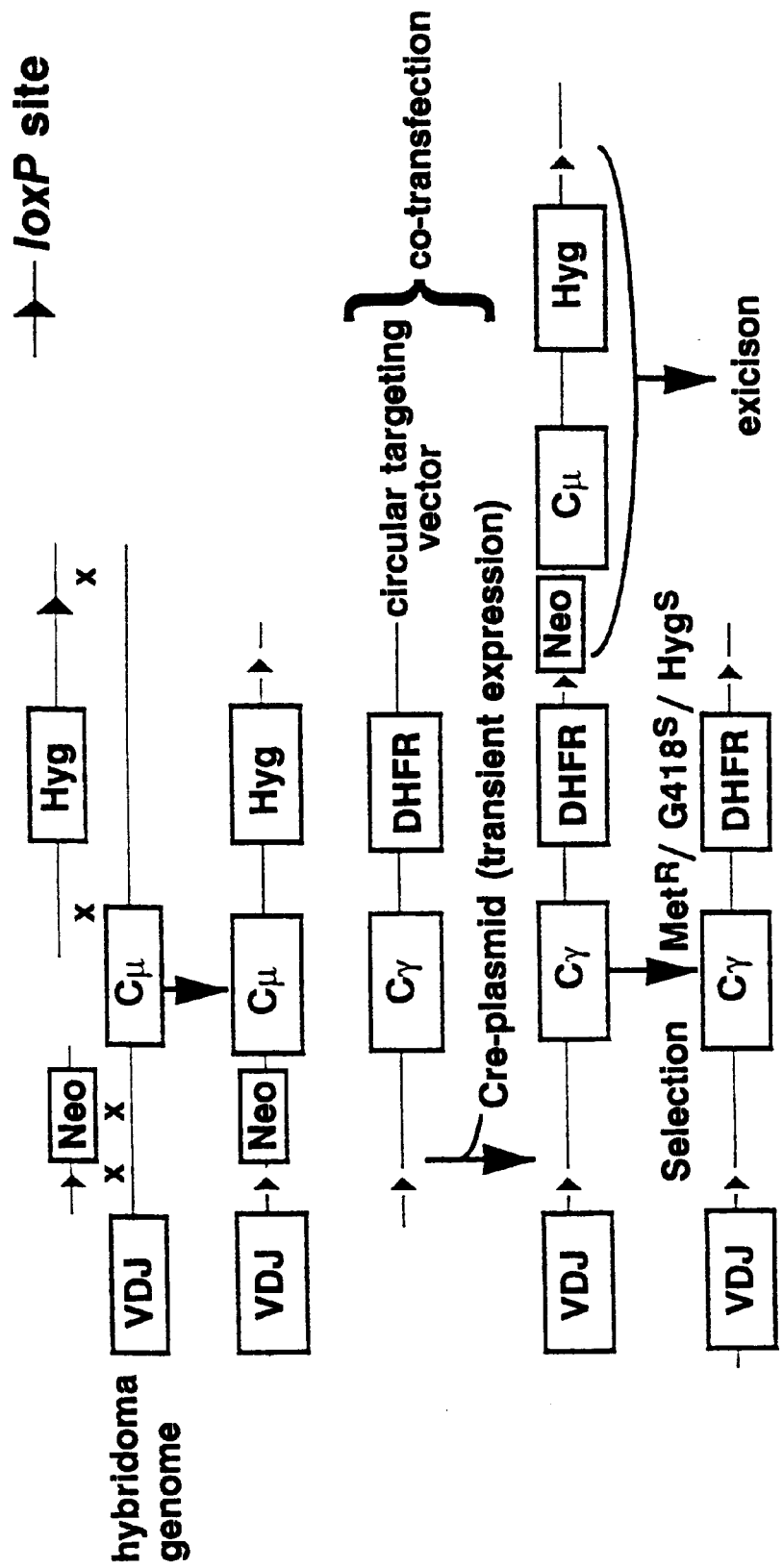
FIG. 2 represents a schematic diagram of another embodiment (Scheme B) of the invention method to produce a cell expressing a human antibody molecule with a modified constant region using Cre-mediated site-specific recombination. This scheme uses two lox sites integrated into the genome of the antibody-producing cell, flanking the constant region to be modified.

FIG. 2 represents a schematic diagram of an alternate embodiment (Scheme B) of the invention method to produce a cell expressing a human antibody molecule with a modified constant region using Cre-mediated site-specific recombination and two lox sites in the genome of the antibody-producing cell. This method comprises inserting, via site-specific homologous recombination, two lox sites flanking the constant region gene of the genomic sequence (human $C_\mu$) which is to be converted to a modified constant region (human $C_\gamma$). As shown in FIG. 2, the cells are sequentially transfected or cotransfected with two homology-targeting vectors, one for inserting each of the two lox sites. Each vector used for insertion of a lox site contains a different selectable marker gene, as illustrated in FIG. 2 by use of the hyg selectable marker gene (i.e., selection for resistance to the hygromycin, "$Hyg^R$") and the neo selectable marker gene (i.e., selection for resistance to the drug G418, indicated as "$G418^R$"). Recombinants with both lox sites inserted are obtained by selecting for both markers, either consecutively or concurrently. In any event the result of proper integration of the two homology-targeting vectors is that the two inserted lox sites flank the gene which is to be converted ($C_\mu$) and each selectable marker gene used for lox site insertion is also flanked by the inserted lox sites.

A vector (comprised of a circular DNA) comprising an additional lox site, the modifying sequence ($C_\gamma$) and a third selectable marker gene (DHFR) is then transfected into the cells, and the lox sites are interacted with Cre. Cre is provided by cotransfecting a vector which transiently expresses a cre gene, as described above. The modifying sequence inserts into the genomic sequence with the second selectable marker gene, via Cre-mediated site-specific recombination of the lox site and the vector and one or the other of the lox sites inserted in the genomic sequence. As illustrated in FIG. 2, integration of the modifying sequence at the lox site adjacent to the constant region gene to be converted ($C_\mu$) is followed in some cells by excision of the first marker gene (hyg), the second marker gene (neo) and the gene to be converted ($C_\mu$), via further Cre-mediated site-specific recombination. Therefore, the desired transfectants are obtained by selecting for a transfectant expressing the third marker gene (DHFR) and not expressing the first or second marker genes, i.e., resistance to methotrexate ("$Met^R$") and sensitivity to the drug G418 ("$G418^S$") and to hygromycin ("$Hyg^S$"), in FIG. 2.

A mutated version of the dihydrofolate reductase gene (*DHFR), which was originally described by Simonsen and Levinson (1983, Proc. Natl. Acad. Sci. U.S.A., 80:2495–2499) as having a lower affinity for the drug methotrexate than does the wild type gene, is used for selection in cells which retain the normal DHFR gene. Stepwise increase of methotrexate concentration is used to effect the genetic amplification of both DHFR and linked genes with concomitant increase in production of protein encoded by the linked gene. Thus, the mutated DHFR marker gene offers the advantage of boosting levels of immunoglobulin production via gene amplification.

EXAMPLE 2

Figure 3:
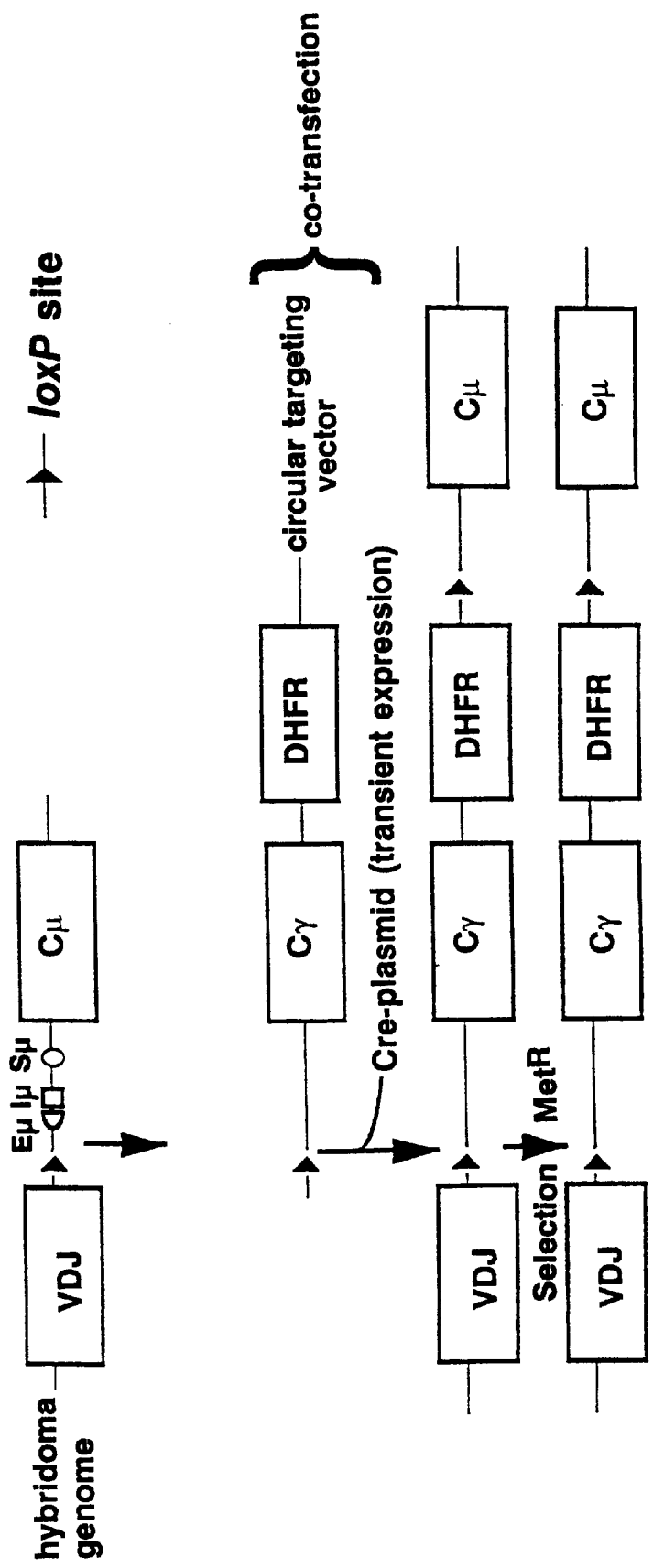
FIG. 3 represents a schematic diagram of one embodiment (Scheme C) of the invention method to produce a cell expressing a human antibody molecule with a modified constant region using Cre-mediated site-specific recombination. This scheme also requires insertion of only a single lox site adjacent to the constant region gene to be modified. However, the lox site is inserted into the genome of a transgenic animal from which the cell expressing the antibody is obtained.

"Class-Switching" of Human Antibodies Produced in Murine Hybridoma Cells Comprising an Integrated Lox Site FIG. 3 represents a schematic diagram of yet another embodiment (Scheme C) of the invention method to produce a cell expressing a human antibody molecule with a modified constant region using Cre-mediated site-specific recombination. The cell to be modified is from a lymphoid cell line (hybridoma) with a genome containing a human constant region gene which is to be converted to a modified constant region. The first lox site is integrated adjacent to the constant region gene (human $C_\mu$) which is to be converted to a modified constant region (human $C_\gamma$). More particularly, Scheme C shows a lox site 5' to the $C_\mu$ enhancer sequences ($E_\mu$), the sequence of $C_\mu$ exon "I" ($I_\mu$) and $C_\mu$ switch sequences ($S_\mu$) of the human $C_\mu$ region.

Such cell lines may be generated, for instance, by transformation of murine hybridomas with vectors containing human constant region genes which are integrated using homologous recombination methods such as described by Fell, et al., supra, where the constant region genes in the vector have been modified by insertion of the lox site by any conventional genetic engineering method. Such cell lines also may be produced by making hybridomas of B-cells from transgenic mice which contain the lox site integrated into germ line DNA as described hereinabove, by conventional hybridoma production methods.

The invention method in Scheme C requires integration of only a single lox site adjacent to the constant region gene to be modified. In this scheme, a vector (comprised of a circular DNA) comprising a second lox site and a selectable marker gene (e.g., DHFR) is transfected into the cells, and the lox sites are transiently interacted with Cre, as described above. Cre-mediated site-specific recombination of the lox site in the genome with the lox site on the circular vector results in insertion into the genome of the modifying sequence ($C_\gamma$) with the selectable marker gene (DHFR). The desired transfectants, which have two lox sites flanking the DHFR and $C_\gamma$ genes, are stable in the absence of further Cre expression and are obtained by selecting for expression of the DHFR marker gene (i.e. resistance to the drug methotrexate indicated as "$Met^R$" in FIG. 3). Verification of the desired modifications of the immunoglobulin loci after each transfection and selection step is provided by conventional genetic analyses, such as by PCR amplification, as above.

What is claimed is:

1. A method to produce an antibody-producing cell comprising a genomically-integrated modified immunoglobulin locus, the method comprising the steps of:
   (a) transfecting a murine embryonic stem (ES) cell in vitro with a first homology-targeting vector comprising:
       (i) a first lox site, and
       (ii) a targeting sequence homologous to a first DNA sequence 5' of a region of a genomically-integrated immunoglobulin locus,
   so that said first lox site is inserted 5' of said region of said immunoglobulin locus via homologous recombination with genomic DNA without disrupting expression of or substantially altering an amino acid sequence of an antibody chain encoded by the immunoglobulin locus;
   (b) generating a transgenic mouse from the ES cell;
   (c) immunizing the transgenic mouse with an antigen;
   (d) isolating an antibody-producing cell from the immunized transgenic mouse;
   (e) transfecting said antibody-producing cell in vitro with a lox-targeting vector comprising:
       (i) a second lox site suitable for Cre-mediated recombination with said first lox site, and
       (ii) a modifying sequence;
   (f) interacting the lox sites with Cre, so that said modifying sequence inserts into said immunoglobulin sequence via Cre-mediated site-specific recombination of said lox sites, thereby forming a modified immunoglobulin locus; and
   (g) selecting a transfectant comprising said modified immunoglobulin locus, which transfectant produces a functional antibody molecule.

2. The method of claim 1 wherein said lox-targeting vector further comprises a selectable marker gene operably linked to control regions such that said marker gene is expressed in said cell,
   so that in step (f), on interacting the lox sites with Cre, said marker gene and said modifying sequence insert into said immunoglobulin locus via Cre-mediated site-specific recombination of said lox sites, and
   in step (g), said selecting for a transfectant comprises selecting for a transfectant expressing said marker gene.

3. The method of claim 1 further comprising
   an additional step before step (e) which additional step comprises transfecting said cell in vitro with a second homology-targeting vector comprising:
       (i) a third lox site suitable for Cre-mediated recombination with said first and second lox sites,
       (ii) a first selectable marker gene operably linked to control regions such that said first marker gene is expressed in said cell, and
       (iii) a targeting sequence homologous to a second DNA sequence adjacent said region of the immunoglobulin locus, said region being flanked by said first and second DNA sequences, so that said third lox site and said first marker gene are inserted into said immunoglobulin locus via site-specific homologous recombination with genomic DNA; and
   wherein in step (e), said lox-targeting vector further comprises a second selectable marker gene operably linked to control regions such that said second marker gene is expressed in said cell,
   so that in step (f), on interacting the lox sites with Cre, said second marker gene and said modifying sequence insert into said immunoglobulin locus via Cre-mediated site-specific recombination of said lox sites; and in step (g), said selecting for a transfectant comprises selecting for a transfectant expressing said second marker gene.

4. The method of claim 3 wherein in step (f), on interacting the lox sites with Cre, after said modifying sequence and second marker gene insert into said immunoglobulin locus, said first marker gene and said region are deleted by Cre-mediated site-specific recombination; and in step (g) said selecting for a transfectant further comprises selecting for a transfectant not expressing said first marker gene.

5. The method of claim 1 wherein said modifying sequence comprises a regulatory nucleotide sequence which replaces all or a portion of a regulatory sequence of the immunoglobulin locus to provide modified expression of said immunoglobulin locus.

6. The method of claim 1 wherein said modifying sequence comprises a nucleotide sequence that encodes a translation product to replace all or a portion of either a constant region or a variable region of the immunoglobulin locus to form an immunoglobulin locus encoding A modified antibody molecule.

7. The method of claim 1 wherein said region of the immunoglobulin locus comprises a constant region gene and said modifying sequence comprises a nucleotide sequence that encodes a translation product to replace all or a portion of the constant region.

8. The method of claim 7 in which said constant region gene comprises a heavy chain gene.

9. The method of claim 7 wherein said constant region gene is a murine constant region gene and said modifying sequence comprises a human constant region gene or portion thereof.

10. The method of claim 7 wherein said constant region gene is a human constant region gene and said modifying sequence comprises a different human constant region gene or portion thereof.

11. The method of claim 7 wherein said constant region gene is a human $C_\mu$ gene and said modifying sequence comprises a human $C_\gamma$ constant region gene.

12. The method of claim 7 wherein said modifying sequence comprises a sequence encoding an enzyme, toxin, hormone, growth factor or linker.

13. The method of claim 1 wherein said antibody-producing cell produces a human antibody.

14. An antibody-producing cell expressing a genomic sequence encoding an antibody, the genomic sequence comprising a modified immunoglobulin locus which comprises a lox site 5' of a modified region in said locus wherein said cell is obtainable by the method of claim 1.

15. A method to produce an antibody from an antibody-producing cell expressing a genomic sequence encoding an antibody, the genomic sequence comprising a modified immunoglobulin locus wherein said cell is obtainable by the method of claim 1, which method comprises:

(a) incubating said cell under conditions such that said cell produces said antibody, and (b) recovering said antibody produced by said cell.

16. A method to produce an antibody-producing cell expressing a genomic sequence encoding an antibody, the genomic sequence comprising a lox site adjacent or integrated within a region of an immunoglobulin locus which method comprises:

(a) transfecting a murine embryonic stem (ES) cell in vitro with a first homology-targeting vector comprising:

(i) a first lox site; and (ii) a targeting sequence homologous to a first DNA sequence 5' of a region of a genomically-integrated immunoglobulin locus, wherein said first lox site is inserted 5' of said region of said immunoglobulin locus via homologous recombination with genomic DNA without disrupting expression of or substantially altering an amino acid sequence of an antibody chain polypeptide encoded by the immunoglobulin locus; and (b) generating a transgenic mouse from the ES cell;

(c) immunizing the transgenic mouse with an antigen;

(d) isolating an antibody-producing cell from the immunized transgenic mouse, wherein the antibody-producing cell comprises said lox site inserted into said genomic DNA 5' of said region.

17. An antibody-producing cell comprising a genomic sequence encoding an antibody molecule, the genomic sequence comprising a lox site 5' of a region of an immunoglobulin locus, wherein said cell is obtainable by the method of claim 16.

18. A method to modify a region of a genomically-integrated immunoglobulin locus of an antibody producing cell, which method comprises:

(a) transfecting the cell isolated in step (d) of claim 16 with a lox-targeting vector comprising:

(i) a second lox site suitable for Cre-mediated recombination with said first lox site, and (ii) a modifying sequence;

(b) interacting the lox sites with Cre, so that said modifying sequence inserts into said immunoglobulin locus via Cre-mediated site-specific recombination of said lox sites, thereby forming a modified immunoglobulin locus; and (c) selecting a transfectant comprising said modified immunoglobulin locus, which transfectant encodes a functional antibody molecule.

19. An antibody-producing cell comprising a genomically-integrated modified immunoglobulin locus which comprises a lox site 5' of a modified region in said locus, wherein said cell is obtainable by the method of claim 18.

20. A method to produce an antibody from a cell comprising a genomically-integrated modified immunoglobulin locus wherein said cell is obtainable by the method of claim 18, which method comprises:

(a) incubating said cell under conditions such that said cell expresses a genomically-integrated modified immunoglobulin locus, thereby producing an antibody, and (b) recovering said antibody produced by said cell.

21. A method to produce an antibody-producing hybridoma, which hybridoma expresses an antibody chain encoded by a modified immunoglobulin locus, the method comprising the steps of:

immunizing a transgenic mouse with an antigen, wherein the mouse is transgenic for a sequence encoding a first lox site, which lox site is present within an immunoglobulin sequence selected from:

(i) a heavy chain polypeptide encoding sequence, wherein the first lox site is positioned 5' of a sequence encoding a heavy chain constant region and 3' of a sequence encoding a heavy chain variable region; and (ii) a light chain polypeptide encoding sequence, wherein the first lox site is positioned 5' of a sequence encoding a light chain constant region and 3' of a sequence encoding a light chain variable region;

wherein the first lox site is positioned within the immunoglobulin sequence such that the encoded polypeptide retains sufficient functionality for production of a functional antibody;

producing hybridomas from antibody-producing cells of the immunized transgenic mouse;

identifying a hybridoma producing an antibody having a desired antigen-binding characteristic;

transfecting the hybridoma in vitro with a lox-targeting vector comprising:

(i) a second lox site suitable for Cre-mediated recombination with said first lox site, and (ii) a modifying sequence;

interacting the lox sites with Cre, so that said modifying sequence inserts into the immunoglobulin sequence via Cre-mediated site-specific recombination at the lox sites, wherein a sequence positioned 3' of the first lox site is displaced by the modifying sequence, producing a modified immunoglobulin locus; and selecting a transfectant having a modified immunoglobulin locus and producing an antibody chain polypeptide from the modified immunoglobulin locus;

wherein a hybridoma expressing an antibody chain encoded by a modified immunoglobulin locus is produced.

22. The method of claim 21, wherein the immunoglobulin sequence having the first lox site is a heavy chain polypeptide-encoding sequence and the modifying sequence is a heavy chain constant region.

23. The method of claim 21, wherein the immunoglobulin sequence having the first lox site is a light chain polypeptide-encoding sequence and the modifying sequence is a light chain constant region.

24. A method to produce an antibody comprising an antibody heavy chain encoded by a modified heavy chain polypeptide-encoding sequence, the method comprising the steps of:

immunizing a transgenic mouse with an antigen, wherein the mouse is transgenic for a sequence encoding a first lox site, which first lox site is present within a heavy chain polypeptide encoding sequence and is positioned 5' of a sequence encoding a heavy chain constant region and 3' of a sequence encoding a heavy chain variable region, said positioning being such that the heavy chain polypeptide retains sufficient functionality for production of a functional antibody;

producing hybridomas from antibody-producing cells of the immunized transgenic mouse;

identifying a hybridoma producing an antibody having a desired antigen-binding characteristic;

transfecting the hybridoma in vitro with a lox-targeting vector comprising:

(i) a second lox site suitable for Cre-mediated recombination with said first lox site, and (ii) a modifying sequence;

interacting the lox sites with Cre, so that said modifying sequence inserts into the heavy chain polypeptide-encoding sequence via Cre-mediated site-specific recombination at the lox sites, wherein all or a portion of the sequence encoding the heavy chain constant region 3' of the first lox site is displaced by the modifying sequence, producing a modified heavy chain polypeptide-encoding sequence; and selecting a transfectant having a modified heavy chain polypeptide-encoding sequence and expressing a modified heavy chain polypeptide;

wherein a hybridoma expressing an antibody comprising a modified heavy chain polypeptide is produced.

25. The method of claim 24, wherein the modifying sequence is a heavy chain constant region.

26. A method to produce an antibody comprising an antibody light chain encoded by a modified light chain polypeptide-encoding sequence, the method comprising the steps of:

immunizing a transgenic mouse with an antigen, wherein the mouse is transgenic for a sequence encoding a first lox site, which first lox site is present within a light chain polypeptide encoding sequence and is positioned 5' of a sequence encoding a light chain constant region and 3' of a sequence encoding a light chain variable region, said positioning being such that the light chain polypeptide retains sufficient functionality for production of a functional antibody;

producing hybridomas from antibody-producing cells of the immunized transgenic mouse;

identifying a hybridoma producing an antibody having a desired antigen-binding characteristic;

transfecting the hybridoma in vitro with a lox-targeting vector comprising:

(i) a second lox site suitable for Cre-mediated recombination with said first lox site, and (ii) a modifying sequence positioned adjacent the second lox site;

interacting the lox sites with Cre, so that said modifying sequence inserts into the light chain polypeptide-encoding sequence via Cre-mediated site-specific recombination at the lox sites, wherein all or a portion of the sequence encoding the light chain constant region 3° of the first lox site is displaced by the modifying sequence, producing a modified light chain polypeptide-encoding sequence; and selecting a transfectant having a modified light chain polypeptide-encoding sequence and expressing a modified light chain polypeptide;

wherein a hybridoma expressing an antibody comprising a modified light chain polypeptide is produced.

27. The method of claim 24, wherein the modifying sequence is a light chain constant region.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: DNA (genomic)

```
       (xi) SEQUENCE DESCRIPTION: SEQ ID NO:1:

ATAACTTCGT ATAATGTATG CTATACGAAG TTAT                                    34

(2) INFORMATION FOR SEQ ID NO:2:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:2:

ACAACTTCGT ATAATGTATG CTATACGAAG TTAT                                    34

(2) INFORMATION FOR SEQ ID NO:3:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

ATAACTTCGT ATAATGTATA CTATACGAAG TTAT                                    34
```